United States Patent [19]

Mirabelli et al.

[11] Patent Number: 5,639,595
[45] Date of Patent: Jun. 17, 1997

[54] IDENTIFICATION OF NOVEL DRUGS AND REAGENTS

[75] Inventors: Christopher K. Mirabelli, Dover, Mass.; David J. Ecker, Leucadia, Calif.; Timothy A. Vickers, Oceanside, Calif.; Debra L. Robertson, Del Mar, Calif.

[73] Assignee: Isis Pharmaceuticals, Inc., Carlsbad, Calif.

[21] Appl. No.: 161,281

[22] Filed: Dec. 2, 1993

Related U.S. Application Data

[63] Continuation-in-part of Ser. No. 517,240, May 1, 1990, abandoned.

[51] Int. Cl.$^6$ .............................. C12Q 1/70; C12Q 1/68; C07H 21/02; C07H 21/04
[52] U.S. Cl. .............................. 435/6; 435/5; 435/172.3; 536/24.1; 536/24.3; 536/24.32
[58] Field of Search .............................. 435/5, 6, 172.3; 536/24.1, 24.3, 24.32

[56] References Cited

U.S. PATENT DOCUMENTS

| | | | |
|---|---|---|---|
| 4,689,320 | 8/1987 | Kaji | 514/44 |
| 5,217,889 | 6/1993 | Roninson et al. | 435/172.3 |
| 5,270,170 | 12/1993 | Schatz et al. | 435/7.37 |

FOREIGN PATENT DOCUMENTS

| | | |
|---|---|---|
| WO86/05803 | 10/1986 | WIPO. |
| WO91/19813 | 12/1991 | WIPO. |
| WO92/00091 | 1/1992 | WIPO. |
| WO92/07071 | 4/1992 | WIPO. |
| WO92/14842 | 9/1992 | WIPO. |
| WO93/04204 | 3/1993 | WIPO. |
| WO93/05182 | 3/1993 | WIPO. |

OTHER PUBLICATIONS

Groger et al. (1989) Directional antisense and sense cDNA cloning using Epstein–Barr virus episomal expression vectors. Gene 81:285.

Sambrook et al. (1989) Molecular Cloning: a laboratory manual, Chapter 11 Cold Spring Harbor, NY: Cold Spring Harbor Laboratory Press.

Weintraub et al., "Anti–sense RNA as a Molecular Tool for Genetic Analysis", *TIG 1:* 22–25 (1985).

Oliphant et al., "Cloning of Random–Sequence Oligodeoxynucleotides", *Gene 44:* 177–183 (1986).

Hasler et al., "A Rapid, Quantitative Bioassay Based on the Human Immunodeficiency Virus *Trans–Activator,*" *Cancer and Infectious Diseases Research:* 507–516 (1989).

Zon, "Oligonucleotide Analogues as Potential Chemotherapeutic Agents," *Pharmaceutical Research* vol. 5, No. 9: 539–547 (1988).

Marcus–Sekura, "Techniques for Using Antisense Oligodeoxyribonucleotides to Study Gene Expression," *Analytical Biochemistry* vol. 172: 289–295 (1988).

Stein et al., "Oligodeoxynucleotides as Inhibitors of Gene Expression: A Review," *Cancer Research* vol. 48: 2659–2668 (13 May 1988).

*Primary Examiner*—Jasemine C. Chambers
*Assistant Examiner*—Scott D. Priebe
*Attorney, Agent, or Firm*—Woodcock Washburn Kurtz Mackiewicz & Norris

[57] ABSTRACT

Methods for identifying oligonucleotides having a desired activity in vivo are disclosed. In accordance with preferred embodiments, oligonucleotides capable of conferring a desired phenotype are identified. Therapeutic, diagnostic and research methods and compositions employing such oligonucleotides are provided. Prior knowledge of the sequence or structure of a target molecule is generally not required.

22 Claims, 5 Drawing Sheets

IDENTIFICATION OF NOVEL DRUGS AND REAGENTS

CROSS REFERENCE TO RELATED APPLICATIONS

This application is a continuation-in-part of U.S. Ser. No. 07/517,240 filed May 1, 1990, now abandoned.

FIELD OF THE INVENTION

This invention relates to the identification, preparation and use of novel therapeutic, diagnostic and research compositions and to methods for their use. More particularly, this invention relates to novel oligonucleotide compositions which can act in vivo such as by the interaction with one or more target molecules to affect the function and to cause changes in biological activity thereby. Methods for identifying such oligonucleotide compositions in vivo are provided which lead to novel therapeutic, diagnostic and research compositions and to methods for diagnosis, treatment and experimentation.

BACKGROUND OF THE INVENTION

Oligonucleotides have recently become accepted as therapeutic moieties in the treatment of disease states in animals and man. For example, workers in the field have now identified antisense, triplex, mimetic or "decoy" and other oligonucleotide therapeutic compositions which are capable of modulating expression of genes implicated in vital, fungal and metabolic diseases.

U.S. Pat. No. 5,098,890 is directed to antisense oligonucleotide therapies for certain cancerous conditions. U.S. Pat. No. 5,135,917 provides antisense oligonucleotides that inhibit human interleukin-1 receptor expression. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods of using them to inhibit HTLV-III replication. U.S. Pat. No. 5,157,115 provides nucleic acid compositions which inhibit or control IL-2 genes by competitively binding to their transcription factors. U.S. Pat. No. 5,176,996 teaches methods for making synthetic oligonucleotides which bind to target sequences in a duplex DNA forming collinear triplexes. Oligonucleotides have been safely administered to humans and several clinical trials are presently underway. It is, thus, established that oligonucleotides can be useful therapeutic instrumentalities and can be configured to be useful in treatment regimes for treatment of cells and animals, especially humans.

One method for inhibiting specific gene expression using oligonucleotides is the antisense approach, in which oligonucleotides are designed to be complementary to a specific target messenger RNA (mRNA), thereby modulating the activity of the mRNA. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which are known to form two hydrogen bonds between them. "Specifically hybridizable" indicates a sufficient degree of complementarity to avoid non-specific binding of the oligonucleotide to non-target sequences. It is understood that an oligonucleotide need not be 100% complementary to its target nucleic acid sequence to be specifically hybridizable.

The relationship between an oligonucleotide and its complementary target nucleic acid is commonly denoted as "antisense." Recent reviews of the antisense field include Uhlmann, E. and A. Peyman (1990) Chem. Reviews 90:544–584; Dolnick, B. J., (1991) Cancer Invest. 9: 185–194; and Stein, C. A. and Y.-C. Cheng (1993) Science 261:1004–1012.

Another approach to oligonucleotide therapeutics is the triplexing (triple-strand) approach, in which oligonucleotides are designed to bind to double-stranded DNA targets, forming triple-stranded structures. Triple helix-forming oligonucleotides are expected to inhibit transcription of the target gene either by inhibition of transcription factor binding or by directly blocking transcription, thereby modulating the expression of the gene. Grigoriev et al., (1993) Proc. Natl. Acad. Sci. U.S.A., 90: 3501–3505.

Oligonucleotides can also be used as "decoys" or mimetics of native DNA or RNA in order to compete with native sequences for binding of specific DNA- or RNA-binding proteins. For example, U.S. Pat. No. 5,157,115 provides nucleic acid sequences which competitively bind regions of the IL-2 or IL-2α genes corresponding to their respective transcription factors. Bielinska et al. disclose inhibition of sequence-specific transcription factor binding with double-stranded oligonucleotides containing known consensus sequences for transcription factor binding. Science 250:997–1000 (1990).

The above approaches are dependent upon a known target sequence, for which a complementary or mimetic oligonucleotide sequence is designed. This approach can be described as a rational drug design approach. Strategies have also been developed for in vitro screening of large populations of random oligonucleotides, by which oligonucleotides having a desired activity such as activity against a preselected target molecule can be identified from a random pool. An advantage of these strategies is that they enable active oligonucleotides to be found whose activity may not have been predicted based purely on the oligonucleotide sequence. This may be because, for example, a target molecule was not known or was not appreciated as a good antisense target, because the active oligonucleotide binds to a region of target secondary structure rather than a linear sequence, or because the "target molecule" is a complex rather than a single molecule. Another advantage is that the target molecule is not limited to nucleic acid, and in fact does not have to be identified at all, as long as a desired activity can be assayed. The desired activity can be, for example, mimetic, catalytic or enzymatic activity in addition to binding activity. Binding is not limited to base-pairing to a complementary target molecule.

Examples of such in vitro random oligonucleotide screening strategies are disclosed in PCT publications WO 93/05182, which discloses an iterative method of determining an oligonucleotide having specific activity for a target biomolecule, and WO 93/04204, which teaches a method for determining an oligomer having specific activity for a target molecule from a pool of random subunits by repeated syntheses of increasingly defined oligomers coupled with selection procedures. PCT publication WO 92/00091 discloses a library of bio-oligomers attached to solid phase supports and use of the library to determine the sequence of a bio-oligomer ligand for an acceptor molecule. PCT publication WO 91/19813 teaches a method for identifying nucleic acid ligands from a mixture of nucleic acids by iterative binding and separation. PCT publication WO 92/14842 discloses isolation of single-stranded DNA oligonucleotide "aptamers" which bind thrombin and inhibit its function in vitro. While these strategies have proven useful in identifying desirable oligonucleotide compounds in vitro, the activity of an oligonucleotide compound measured in vitro may differ from the activity of the same compound in the intracellular microenvironment. It is therefore desirable to screen random oligonucleotides for in vivo activity.

PCT publication WO 86/05803 discloses use of genes at least partially composed of stochastic synthetic polynucleotides and introduced into host cells, and identification of peptides or polypeptides produced, or DNA or RNA sequences incorporated into the host cell genome, which have a desired property. PCT publication W0 92/07071 discloses a method for obtaining genetic suppressor elements for a known gene comprising fragmentation of a DNA sequence homologous to the gene to be suppressed, incorporation of the DNA fragments into vectors, introduction of the vectors into cells, and isolation of genetically modified cells containing genetic suppressor elements.

There has been and continues to be a long-felt need for oligonucleotides which are capable of effective therapeutic and diagnostic use. Further, there is a need for a method of identifying oligonucleotides which have activity in vivo particularly when a target sequence or structure is not defined.

OBJECTS OF THE INVENTION

It is an object of this invention to provide methods for in vivo identification of oligonucleotides which may be useful as drugs.

It is a further object of this invention to provide methods for in vivo identification of oligonucleotides which have desired activity.

A still further object is to provide methods for identification of such oligonucleotides without the need for prior knowledge of the structure or sequence of a target molecule.

It is another object of this invention to provide methods for identifying oligonucleotides useful in therapy of disease states.

A further object is to identify oligonucleotides useful for the determination of the status of bodily functions of animals.

Yet another object is to identify oligonucleotides which are useful as research reagents such as for blocking gene expression of particular RNA molecules.

An additional object of the invention is to identify loci of nucleic acids which control the expression of polypeptides having a significant effect on a bodily function of an animal.

Other objects will become apparent to persons of ordinary skill in the art from a review of the present specification.

SUMMARY OF THE INVENTION

Although oligonucleotides, antisense and otherwise, are currently being investigated as potential therapeutic agents, it is not a simple matter, using rational drug design methods, to select the best possible oligonucleotide sequence to inhibit a particular cellular or viral function. The methods of the present invention overcome these difficulties.

In accordance with this invention, methods are provided for identifying oligonucleotides having in vivo activity comprising providing a plurality of vectors which include substantially randomly sequenced oligonucleotides and incorporating those vectors into cells. The cells are provided with conditions for growth and assayed for the phenotype conveyed by the desired activity. Cells which display this phenotype are then identified. Preferably, the nucleic acid sequence of the included oligonucleotide is determined for those cells having the desired phenotype. In preferred embodiments, the cells are bacterial, fungal or mammalian cells.

In accordance with a preferred embodiment of this invention, methods are provided for identifying oligonucleotides capable of inhibiting an infectious agent comprising providing a plurality of vectors which include substantially randomly sequenced oligonucleotides and incorporating those vectors into cells. The cells are infected with the infectious agent and provided with conditions for growth of the cells. Cells which are resistant to the infection are then identified. Preferably, the nucleic acid sequence of the included oligonucleotide is determined for those cells resistant to the infection. In a more preferred embodiment, the infectious agent is a virus and the cells are mammalian cells, most preferably human cells.

In accordance with another preferred embodiment of this invention, methods are provided for identifying oligonucleotides capable of inhibiting the expression of a cell surface protein comprising providing a plurality of vectors which include substantially randomly sequenced oligonucleotides and incorporating those vectors into cells, preferably mammalian cells. Cells containing oligonucleotides which reduce the expression of the cell surface protein are selected and isolated from the remaining cells. Preferably, the nucleic acid sequence of the included oligonucleotide is determined for those cells which exhibit reduced expression of the protein. In more preferred embodiments, the cell surface protein is an intercellular adhesion molecule, an oncogene product, multidrug resistance protein (MDR) or multidrug resistance-associated protein (MRP).

In accordance with still another preferred embodiment of this invention, methods are provided for identifying oligonucleotides capable of inhibiting the interaction of an activator (protein or nucleic acid) with its responsive region (promoter) on a gene, comprising providing a plurality of vectors which include substantially randomly sequenced oligonucleotides and incorporating those vectors into cells, preferably mammalian cells, into which is also incorporated a plasmid containing a promoter or response region located 5' to a lethal gene and in a transcriptional relationship with the lethal gene. Interaction of the activator protein or nucleic acid with the promoter region would allow the lethal gene to be expressed, causing cell death. Cells containing oligonucleotides which block the interaction of the activator molecule with the promoter survive and are isolated. Preferably, the nucleic acid sequence of the included oligonucleotide is determined for those cells which exhibit reduced expression of the lethal gene.

In other preferred embodiments, this strategy can be used in yeast and other fungal systems. In one such embodiment, methods are provided for identifying oligonucleotides capable of inhibiting adherence of yeast cells to mammalian cells, comprising providing a plurality of vectors which include substantially randomly sequenced oligonucleotides and incorporating those vectors into yeast cells. Yeast cells containing oligonucleotides which cause loss of adherence are selected and isolated from the remaining cells. Preferably, the nucleic acid sequence of the included oligonucleotide is determined for those cells which exhibit reduced adherence. In more preferred embodiments, the mammalian cells are human endothelial cells. In other preferred embodiments oligonucleotides lethal to yeast or other fungi can be determined. A negative selection scheme for inhibition of a particular gene target can be used to determine oligonucleotides which inhibit the desired target gene. In a preferred embodiment, the desired target is an enzyme required for fungal growth, for example 2,3-oxidosqualene cyclase.

In yet another preferred embodiment, oligonucleotides which inhibit gene expression by acting as substrates or mimetics for cellular proteins can be identified. In one such embodiment, methods are provided for identifying otigonucleotides capable of interfering with aminoacylation by particular bacterial tRNA synthetases comprising providing a plurality of vectors which include substantially randomly sequenced oligonucleotides and incorporating those vectors into bacterial cells. Cells are grown on plates supplemented with the relevant amino acid. Cells are replica plated onto plates without the relevant amino acid supplement. Cells containing oligonucleotides which interfere with aminoacylation by the desired tRNA synthetase are nonviable; corresponding colonies can be recovered and isolated from the replica plate. Preferably, the nucleic acid sequence of the included oligonucleotide is determined for those cells which exhibit the nonviable phenotype. Preferably the bacterium is a human pathogen.

In accordance with preferred embodiments, the substantially randomly sequenced oligonucleotides are prepared through solid phase synthesis or otherwise and comprise from about 6 to about 100 nucleic acid subunits, more preferably from about 6 to about 30 nucleic acid subunits. Chemical modifications may be introduced into oligonucleotides to increase their therapeutic activity. Such modifications are designed to increase cell penetration of the oligonucleotides, to stabilize them against nucleases and other enzymes that degrade or interfere with the structure or activity of the oligonucleotides in the body, or to improve their pharmacokinetic properties. As an alternative to synthetic oligonucleotides, cDNA or genomic DNA, preferably from an infectious organism, may be used in the preparation of the vectors. Such DNA is preferably fragmented to provide a plurality of fragmentary portions of the DNA having numbers of subunits in the range of from about 50 to a few thousand with from about 100 to about 1000 being convenient and preferred.

In accordance with other embodiments, reagents are prepared having as at least a component thereof the nucleic acid sequence of the inserted oligonucleotide which has been identified as coming from a cell having the desired phenotype. Therapeutic, diagnostic and research compositions and kits are prepared from such reagents and methods of therapeutics, diagnosis and research employing them are comprehended as being within this invention.

DETAILED DESCRIPTION OF PREFERRED EMBODIMENTS

Figure 1:
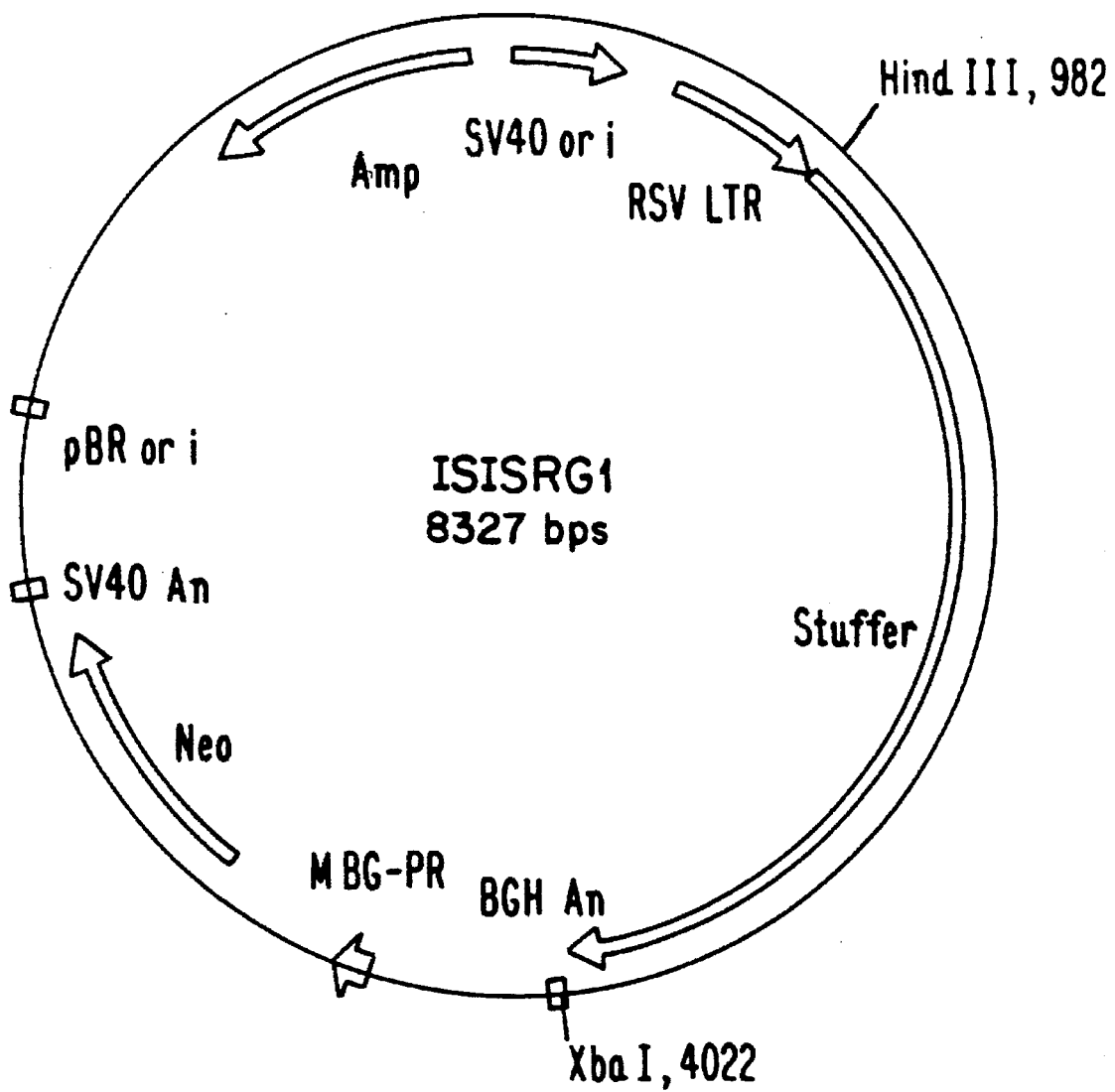
FIG. 1 depicts a schematic structure of the vector ISIS RG-1.

The present invention provides methods of identifying oligonucleotide sequences that display in vivo activity. Expression vectors containing random oligonucleotide sequences formed by chemical synthesis, or derived from DNA, mRNA or cDNA by nuclease treatment, or by shearing, are transformed into cells. The cells are then assayed for a phenotype resulting from the desired activity of the oligonucleotide included within the vector transferred into the identified cells and selected on the basis of the desired phenotype of said cells. For example, the cells do not die, the cells grow at an increased rate, or exhibit other desired behavior.

Once cells with the desired phenotype have been identified, the sequence of the oligonucleotide having the desired activity can be identified. Identification may be accomplished by recovering the vector or by polymerase chain reaction (PCR) amplification and sequencing the region containing the inserted nucleic acid material.

The cells, expression vectors and method of selecting for the oligonucleotide sequence are dependent upon the type of phenotype to be selected for. For example, if it is desired to identify oligonucleotides which inhibit herpesvirus infection, the cell type chosen will be one that can be infected with the herpesvirus, and the expression vector will be one that is compatible with the cell chosen.

In accordance with this invention, the term "random" as applied to nucleic acid sequences has several related meanings. Thus, truly random oligonucleotides formed through solid phase synthesis is included in some aspects of the present invention. However, such random oligonucleotides need not be completely and statistically random in fact and enrichment of oligonucleotides in certain bases may be desired in accordance with some embodiments of this invention.

In accordance with other embodiments of the present invention, the term "random" relates to the use of genomic DNA from an organism, for example from an infectious agent. Such genomic DNA is harvested from the organism in a conventional way and then either sheared or subjected to nuclease digestion to form a plurality of fragments of the DNA. While not truly random in that the parent DNA had a definite sequence, the sequence is generally unknown and its fragmentation is generally uncontrolled.

In accordance with still other aspects of the present invention, the term "random" relates to complementary DNA or cDNA. Complementary DNAs can be prepared for all or some RNAs of an organism, especially an infectious organism. The cDNA may then be inserted into a vector and used as discussed herein. Thus, it will be understood that the use of random oligonucleotides as intended by this invention encompasses all of the foregoing alternatives.

In accordance with methods of the present invention, oligonucleotides are generally of a size as to be effective in the performance of this invention. Generally, oligonucleotides are from about 6 to about 100 bases in length and preferably are from about 6 to about 30 bases are employed when synthetically generated random sequences are employed. Alternatively, from about 50 to a few thousand base units are employed when genomic DNA or cDNA fragments (i.e. oligonucleotides) are employed in accordance with methods of the present invention.

In the context of this invention, the term "oligonucleotide" refers to an oligomer or polymer of ribonucleic acid or deoxyribonucleic acid. This term includes oligomers consisting of naturally occurring bases, sugars and inter-sugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). Also preferred are oligonucleotides having morpholino backbone structures. Summerton, J. E. and Weller, D. D., U.S. Pat. No. 5,034,506. In other preferred embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, Science 1991, 254, 1497. Other preferred oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety, an RNA cleaving group; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and aridine may be used, such as inosine. Any of the above modifications can be used, provided they can be incorporated into random oligonucleotides.

Oligonucleotides for use in the methods of the invention may be obtained from several sources and incorporated into vectors. Random sequences can be prepared by use of a DNA synthesizer to generate a length of DNA with an equimolar mixture of A, G, C, T at each position. Equipment for such synthesis is sold by several vendors including Applied Biosystems. Any other means for such synthesis may also be employed and such synthesis of the oligonucleotides is well within the talents of the routineer. Further, the complementary strand can be generated, for example, using a DNA primer and DNA polymerase. By making DNA ends of the random sequence complementary to the overhangs left by restriction enzyme cleavage it is possible to clone the random mixture into the expression vector.

Alternatively, the DNA of an infectious or other agent may be cut into short pieces by shearing or by treatment with DNase. For example, Herpesvirus DNA may be sheared or DNase treated to produce oligonucleotides of small sizes and "shotgun cloned" into an expression vector. Some of the sequences expressed would be antisense to Herpesvirus genes. In still other embodiments of the present invention a cDNA library from mRNA isolated from infected cells can be created. The cDNA can then be directionally cloned into the expression vector such that RNAs are produced in an antisense orientation. This approach can identify new genes that are key to successful infection. The manipulation of expression vectors and oligonucleotides and the transformation of cells can be performed according to standard techniques such as may be found in Maniatis et al., Molecular Cloning, A Laboratory Manual, Cold Spring Harbor Press, Cold Spring Harbor, N.Y., 1982.

Figure 3:
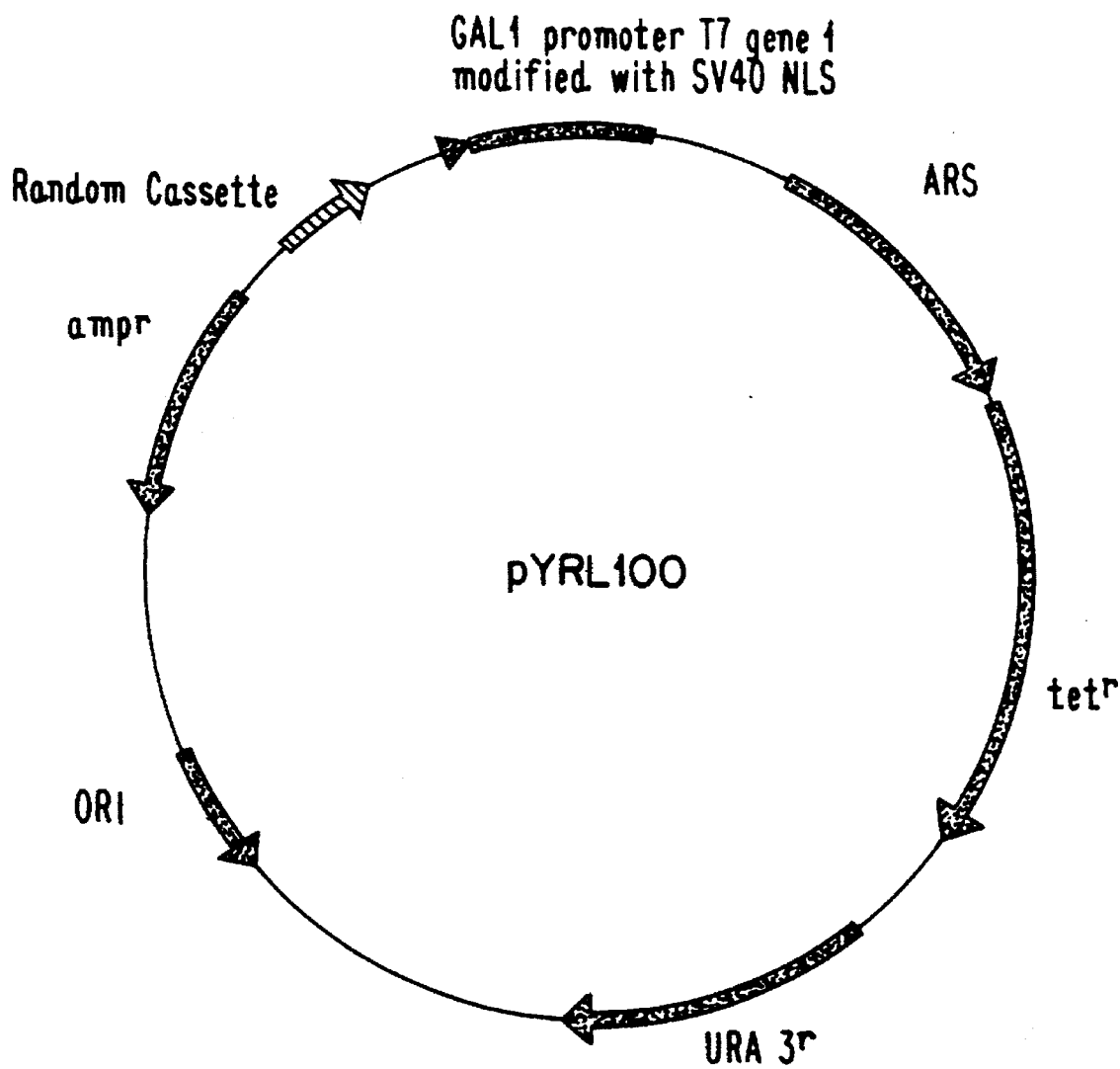
FIG. 3 is a schematic diagram of the vector pYRL100.
Figure 4:
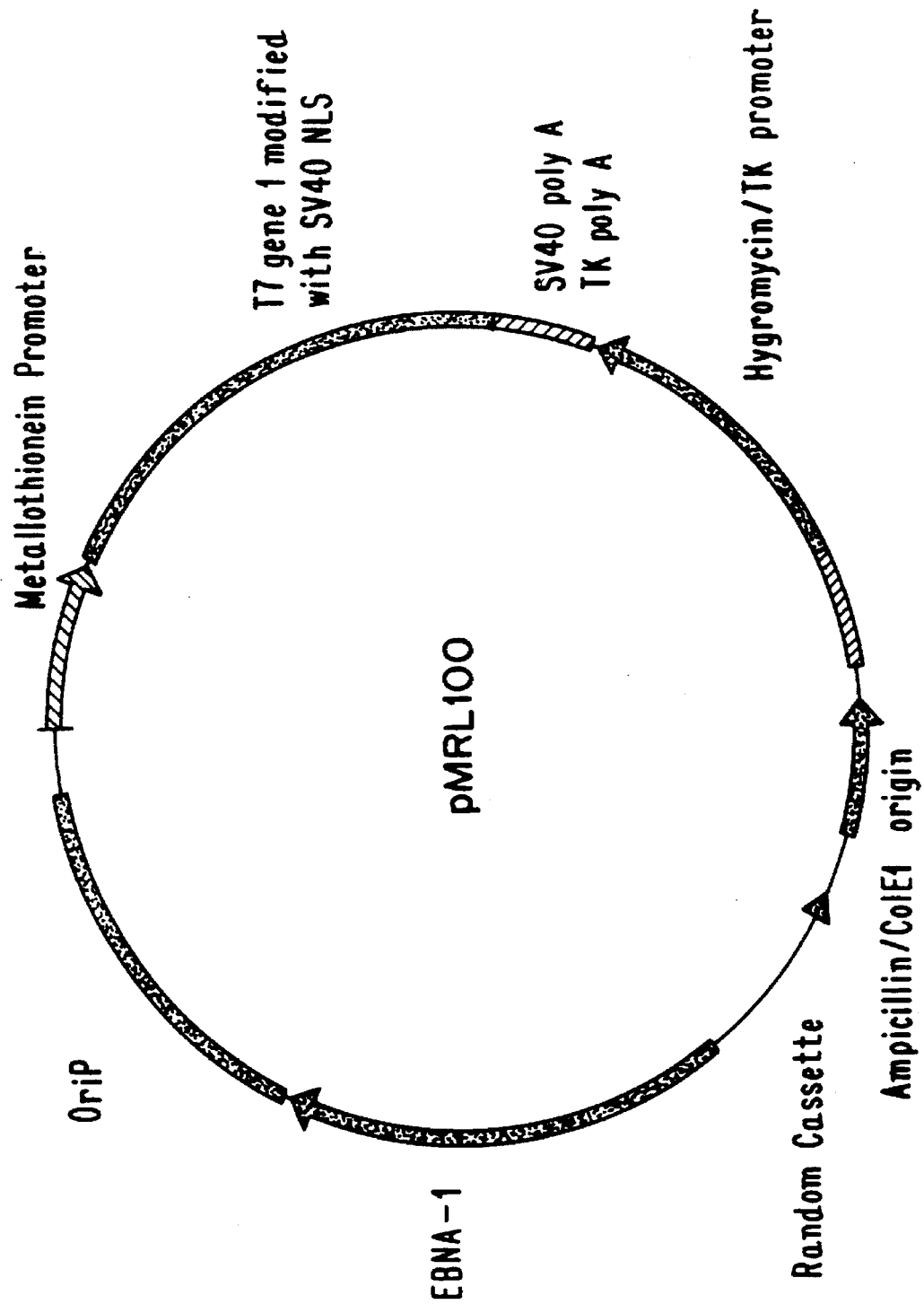
FIG. 4 is a schematic diagram of the vector pMRL100.

Expression vectors suitable for use in the methods of the invention include commercially available plasmid vectors such as pMAMM-NEO (Clontech) and other expression vectors. As will be understood, vectors used depend on type of cell to be transformed. Presently preferred vectors are pARL100 for E. coli host cells (shown in FIG. 2), pYRL100 for yeast host cells (shown in FIG. 3) and pMRL100 for mammalian cells (shown in FIG. 4). Expression from these vectors is inducible by addition of a suitable inducer (for example, galactose) to the growth medium. It is preferred that the plasmid expression vector contain at least one gene to allow construction and recovery of the vector, such as an antibiotic resistance gene, for example the ampicillin resistance gene. It is also preferred that the plasmid expression vector contain an inducible promoter and transcriptional initiation region to express the random or semi-random sequences. A polyadenylation signal or an intron may or may not be included.

A preferred plasmid expression vector is ISIS RG-1 which is illustrated schematically in FIG. 1. This vector contains the neomycin gene for G418 selection of stably transformed cells in culture and the ampicillin gene for bacterial amplification. Inserts can be directionally cloned by cutting at the Hind III and Xba I sites, releasing a stuffer fragment. The Hind III site is immediately 3' to the RSV promoter and the Xba I site is immediately 5' of the bovine growth hormone (BGH) poly (A) site.

Once expression vectors containing oligonucleotides are constructed, the expression vectors are inserted into cells suitable for selecting the phenotype resulting from the desired oligonucleotide activity. Where the phenotype is resistance to an infectious agent, the cells may already be infected with the infectious agent or they may be infected with the infectious agent after insertion of the expression vector. The expression vectors are inserted into the cells by standard methods known to those skilled in the art, for example calcium phosphate transfection or electroporation.

The cells are then cultured and oligonucleotides are expressed in vivo. In some preferred embodiments of the present invention, transcription of random oligonucleotides is directed by the bacteriophage T7 RNA polymerase. It has been demonstrated that the T7 polymerase made during phage infection is capable of directing the transcription of genes cloned in plasmids. Studier, F. W. and J. J. Dunn, Cold Spring Harbor Symp. Quant. Biol. 47:999–1007 (1983).

For example, in an E. coli host, T7 RNA polymerase can direct the transcription of a large amount of specific RNAs by transcribing the DNA adjacent to the T7 promoter. The unmodified T7RNA can transcribe T7 promoter constructs within the cytoplasm of a eukaryotic cell but not those in the cell nucleus. A modified form of the polymerase has been constructed by substituting a sequence encoding the nuclear location signal of the SV40 large T antigen for the N-terminal part of the polymerase. This altered polymerase can enter the nucleus of the host and transcribe hybrid genes containing the T7 promoter. This form of the polymerase allows for stable high levels of expression of specific RNAs in mammalian and fungal cells.

In still other embodiments of the present invention expression cassettes are used for expression of random oligonucleotides. For example, transcription of the random oligonucleotide library by the T7 RNA promoter is used with a termination strategy designed to define the 3' end of the oligonucleotide. Several possible termination strategies can be included in the random oligonucleotide vector cassettes. In one strategy a tRNA sequence is used which is designed to fold into a hairpin structure which is recognized by the endogenous RNase P. This sequence is incorporated into the random oligonucleotide vector downstream (towards the 3' end) of the random insert region. RNase P will cleave the hairpin at a site which generates the random oligonucleotide and the hairpin sequence as products. In another strategy, the T7 RNA polymerase transcribes a DNA template which encodes the random sequence followed by a hammerhead ribozyme sequence. After transcription, the hammerhead is designed to catalyze site-specific cleavage at the 3' end of the random oligonucleotide.

Expression cassettes of this invention have been designed to direct the in vivo transcription and specific termination of any nucleic acid sequence in prokaryotic, fungal and mammalian systems. A generic expression cassette has been designed to allow the in vivo transcription of any DNA template inserted into the expression vector. Preferred inserts may include members of a random oligonucleotide library, cDNAs or fragments thereof, fragments of viral or genomic DNA, catalytic RNA sequences, or short oligonucleotide sequences encoding restriction sites.

In the case of random oligonucleotide libraries, inserts may be of single or variable length, with or without polyadenylation sequences. Table 1 compiles some exemplary expression cassettes prepared in accordance with some of the principals set forth in accordance with this invention. Cassette 1 is an expression cassette sequence for T7 RNA polymerase-directed expression of random RNAs using a tRNA hairpin structure as a terminator. Cassette 2 is an expression cassette sequence for T7 RNA polymerase-directed expression of random RNAs using a ribozyme sequence as a terminator. Cassette 3 is an expression cassette sequence for T7 RNA polymerase-directed expression of random RNAs with a polyadenylation site using a tRNA hairpin structure as a terminator.

When the insert in the expression cassette is cDNA, either from viral or genomic DNA, polyadenylation sites can also be included. Cassette 4 is an expression cassette sequence for T7 RNA polymerase-directed expression of double-stranded cDNA using a tRNA hairpin structure as a terminator. Cassette 5 is an expression cassette sequence for T7 RNA polymerase-directed expression of double-stranded cDNA with polyadenylation sites included, using a tRNA hairpin structure as a terminator.

When the insert in the expression cassette is restriction endonuclease fragments from viral or genomic DNA, polyadenylation sites can also be included. Cassette 6 is an expression cassette sequence for T7 RNA polymerase-directed expression of viral or genomic DNA using a tRNA hairpin structure as a terminator.

Cassette 7 is an expression cassette sequence for T7 RNA polymerase-directed expression of vital or genomic DNA fragments with polyadenylation sites included, using a tRNA hairpin structure as a terminator.

Sequences include dashes which are used merely to separate the functional regions of the sequences; the actual sequences are continuous. Rest. site denotes "restriction site".

| CASSETTE | SEQ ID NO: | SEQUENCE | | | |
|---|---|---|---|---|---|
| #1 | 1 | CCCAGGCCT-<br>Rest. site | TAATACGACTCACTATA-<br>T7 promoter | GGNNNNNNNNNNNNNNN-<br>Random sequence | |
| | | GCCCGGACTCGGTTCGATTCCGAGTCCGGGCACCAC-<br>tRNA terminator | | ATCGATGTC<br>Rest. site | |
| #2 | 2 | CCCAGGCCT-<br>Rest. site | TAATACGACTCACTATA-<br>T7 promoter | GGNNNNNNNNNNNNNNN-<br>Random sequence | |
| | | CGGTCTCACGAGCAAAAGCTCGTCTGATGAGTCCGTGAGGACGAAAGACCG-ATCGATGTC<br>ribozyme terminator | | | Rest. site |
| #3 | 3 | CCCAGGCCT-<br>Rest. site | TAATACGACTCACTATA-<br>T7 promoter | GGNNNNNNNNNNNNNNN-<br>Random sequence | AATAAA-<br>polyA site |
| | | GCCCGGACTCGGTTCGATTCCGAGTCCGGGCACCAC-<br>tRNA terminator | | | ATCGATGTC<br>Rest. site |
| #4 | 4 | CCCAGGCCT-<br>Rest. site | TAATACGACTCACTATA-<br>T7 promoter | GG- cDNA sequences-<br>GG-CDNA sequences | |
| | 5 | GCCCGGACTCGGTTCGATTCCGAGTCCGGGCACCAC-<br>tRNA terminator | | ATCGATGTC<br>Rest. site | |
| #5 | 4 | CCCAGGCCT-<br>Rest. site | TAATACGACTCACTATA-<br>T7 promoter | GG-cDNA sequences-<br>GG-cDNA sequences | |
| | 6 | AATAAA-<br>polyA site | GCCCGGACTCGGTTCGATTCCGAGTCCGGGCACCAC-<br>tRNA terminator | | ATCGATGTC<br>Rest. site |
| #6 | 4 | CCCAGGCCT-<br>Rest. site | TAATACGACTCACTATA-<br>T7 promoter | GG-DNA fragments-<br>GG-DNA fragments | |
| | 5 | GCCCGGACTCGGTTCGATTCCGAGTCCGGGCACCAC-<br>tRNA terminator | | ATCGATGTC<br>Rest. site | |
| #7 | 4 | CCCAGGCCT-<br>Rest. site | TAATACGACTCACTATA-<br>T7 promoter | GG-DNA fragments-<br>GG-DNA fragments- | |
| | 6 | AATAAA-<br>polyA site | GCCCGGACTCGGTTCGATTCCGAGTCCGGGCACCAC-<br>tRNA terminator | | ATCGATGTC<br>Rest. site |

Catalytic RNA sequences or short oligonucleotide sequences encoding restriction sites can also be incorporated using this cassette approach, using one of the termination methods described (tRNA hairpin or ribozyme).

In accordance with methods of the present invention, cells having a desired phenotype are selected for. Selection methods will depend on the type of cell and the phenotype desired. For example, as in Example 1 below in which the desired phenotype is resistance to Herpesvirus infection, neomycin resistant cells can be propagated to confluency in 10 cm tissue culture dishes. When confluency is reached the entire population is infected with HSV-1 at a low MOI. Medium is changed at frequent intervals following the infection to reduce the frequency of secondary infection. Cells which survive the infection are grown to confluency, then infected a second time in the same manner. This process is repeated until all cells survive an infection or until individual resistant colonies are selected. In accordance with some aspects of the present invention, selection for inhibition of viral infection is achieved in mammalian cells. The expression vector containing the random oligonucleotide insert is transfected into a mammalian, preferably human, cell line, using calcium phosphate, electroporation or other standard methods. Oligonucleotides are expressed by induction of the RNA polymerase which directs the transcription of the random insert. Selection occurs when the cells expressing the oligonucleotide are infected with a lytic virus, for example cytomegalovirus or herpes simplex virus. Those cells expressing an active oligonucleotide, i.e., one which confers resistance to the virus, will survive the viral infection. These cells are then recovered and amplified in culture and the oligonucleotides contained within them can be identified by plasmid isolation or PCR amplification and DNA sequencing of clonal populations of individual recovered cells.

In accordance with other preferred embodiments of the present invention, selection for inhibition of expression of a cell surface protein in mammalian cells is performed. Oligonucleotides which inhibit the in vivo expression of a cell surface protein, such as, for example, intercellular adhesion molecules, multidrug resistance proteins such as MDR and MRP, and oncogene products expressed on the cell surface, can be identified using this method. The expression vector containing the random oligonucleotide insert is transfected into a mammalian, preferably human, cell line, using calcium phosphate, electroporation or other standard methods. Where an oncogene product is the cell surface protein to be inhibited, the cell line is preferably a transformed cell line. Oligonucleotides are expressed by inducing the RNA polymerase which directs the transcription of the random insert. Individual cells expressing sequences which reduce the expression of the cell surface protein can be isolated from the remaining population using a selective antibody killing assay. This assay takes advantage of the antibody-mediated complement lysis reaction. Cells that express the protein on the cell surface will be eliminated by lysis following addition of antibody to the protein, and complement. Hood, L. E., Weissman, I. L., and W. B. Wood. *Immunology* pp. 161–164; Benjamin/Cummings Publishing Co., Inc., 1978. This allows the recovery of those cells in which expression of the cell surface protein has been inhibited by oligonucleotide. These cells are then recovered and amplified in culture and the oligonucleotides contained within them can be identified by plasmid isolation or PCR amplification and DNA sequencing of clonal populations of individual recovered cells.

In accordance with other aspects of the present invention selection of oligonucleotides that inhibit the interaction of activator (protein or nucleic acid) with responsive region (promoter) in mammalian cells can be performed. Negative selection can be used to select oligonucleotide sequences that inhibit the interaction of an activator (protein or nucleic acid) with a responsive region (promoter). The promoter or responsive region is cloned into a plasmid at a position 5' to a lethal gene, such as Diphtheria toxin-A, and in a transcriptional relationship to the lethal gene. The expression vector containing the random oligonucleotide insert and the lethal gene vector are cotransfected into a mammalian, preferably human, cell line, using calcium phosphate, electroporation or other standard methods. Oligonucleotides and lethal gene are expressed by inducing the RNA polymerase which directs the transcription of the insert in each plasmid. Interaction of the activator with the promoter element will allow the expression of the lethal gene and cell death will occur. Active oligonucleotide which block the interaction of the activator molecule with the promotor will prevent expression of the lethal gene and the cell will live. These cells are then recovered and amplified in culture and the oligonucleotides contained within them can be identified by plasmid isolation or PCR amplification and DNA sequencing of clonal populations of individual recovered cells.

Yeast and other fungal systems may also be useful as selection modalities in some aspects of the present invention. For example, oligonucleotides that inhibit cell adhesion may be selected for, such as activity against an integrin. Thus, in accordance with some embodiments of the present invention, the expression vector containing the random oligonucleotide insert is transfected into yeast spheroplasts using calcium phosphate, electroporation or other standard methods. Oligonucleotides are expressed by inducing the RNA polymerase which directs the transcription of the random insert. Yeast cells are incubated on confluent layers of human umbilical vein endothelial cells. Selection occurs when the cells expressing the active oligonucleotide are unable to adhere to the endothelial cells. Nonadherent cells are isolated from the remaining population by washing the endothelial cells with saline. These nonadherent yeast cells are then recovered and amplified in culture and the oligonucleotides contained within them are identified by plasmid isolation or PCR amplification and DNA sequencing of clonal populations of individual recovered cells.

In accordance with other aspects of the present invention, oligonucleotides that are lethal to yeast may be selected for. Thus, in some embodiments of the present invention, an expression vector containing the random oligonucleotide insert is transfected into yeast spheroplasts using calcium phosphate, electroporation or other standard methods. Cells are initially grown in the absence of the inducer (galactose) for the expression vector, and then replica plated onto plates containing the inducer. Oligonucleotides are expressed by inducing the RNA polymerase which directs the transcription of the random insert. Colonies containing active oligonucleotides will die; matching colonies are recovered from the master plate, amplified in culture and the oligonucleotides contained within them are identified by plasmid isolation and DNA sequencing.

Selection for the inhibition of a targeted gene by negative selection in yeast may also be performed in accordance with methods of the present invention. Oligonucleotides which inhibit a particular gene can be isolated using this method, provided that appropriate selection is available. For example, the enzyme 2,3-oxidosqualene cyclase (ERG7) catalyzes the conversion of 2,3-oxidosqualene to lanosterol in the ergosterol biosynthesis pathway of fungi. The expression vector containing the random oligonucleotide insert is transfected into yeast spheroplasts using calcium phosphate, electropotation or other standard methods. Cells are initially grown in the presence of ergosterol supplementation, and then replica plated onto plates without ergosterol. Oligonucleotides are expressed by inducing the RNA polymerase which directs the transcription of the random insert. Colonies containing active oligonucleotides will die; matching colonies are recovered from the master plate, amplified in culture and the oligonucleotides contained within them are identified by plasmid isolation or PCR amplification and DNA sequencing.

Bacterial cell systems may also be effective selection modalities in accordance with some methods of the present invention. Thus, selection of oligonucleotides that inhibit gene expression by acting as substrates for cellular proteins may be performed. One example of this method is selection of oligonucleotides which can be used as substrates for aminoacylation by tRNA synthetases. In preferred embodiments, bacterial cells are used. For example, *E. coli* cells are transformed with the expression vector library using standard methods. Cells are initially grown on plates supplemented with target amino acid. Colonies are then replica-plated onto plates without amino acid supplementation. Oligonucleotides are expressed by inducing the RNA polymerase which directs the transcription of the random insert. Colonies containing active oligonucleotides which interfere with aminoacylation will die; matching colonies are recovered from the master plate, amplified in culture and the oligonucleotides contained within them are identified by plasmid isolation or PCR amplification and DNA sequencing.

Selection of oligonucleotides that inhibit expression of a particular target gene (β-galactosidase) in bacteria is still another selection system useful in methods of the present invention. The *E. coli* enzyme β-galactosidase was chosen as a target for oligonucleotide inhibition using this method. A random oligonucleotide library of 2.7×10$^8$ chemically synthesized 14 mer sequences was cloned into a T7 RNA polymerase expression plasmid containing the targeted gene. The expression of β-galactosidase is measured by measuring the ability of the host cell to process the exogenous substrate X-gal (5-bromo-4-chloro-3-indolyl-β-D-galactoside). A functional β-galactosidase enzyme confers a blue color to the host cell or colony in the presence of X-gal. Inhibition of the enzyme generates a white colony. White colonies are then picked and amplified.

Once cells with the desired phenotype have been selected, the sequences of the oligonucleotides contained within those cells are determined. Plasmids containing active oligonucleotides are isolated by standard plasmid recovery methods or, alternatively, inserts may be amplified using suitable PCR primers. Holmes, D. S. and M. Quigley, Anal. Biochem. 114:193 (1981). Inserts are sequenced using standard sequencing methods, such as the Sanger dideoxy sequencing method. Sanger, F., Nicklen, S. and A. R. Coulsen. Proc. Natl. Acad. Sci. 74:5463–5467 (1977).

Active oligonucleotide sequences can be subsequently used to design other active compounds through sequence modification ("molecular evolution") and/or chemical modification, for example to improve stability and uptake properties of the oligonucleotide.

The following examples are illustrative and are not meant to be limiting of the present invention.

EXAMPLES

Example 1

Vector Construction

The following method describes a scheme to generate random and semi-random antisense messages to screen for sequences which specifically inhibit HSV infection of mammalian cells in culture. This may be done by three different means. 1) random-synthetic oligonucleotides of defined length, 2) random oligonucleotides produced by shearing genomic DNA, and 3) a random cDNA library generated from HSV infected cells. In each case the vector used will be ISIS RG-1. ISIS RG-1 is derived from pSV2A replacing the SV40 promoter of pSV2A with an RSV promoter. Kadesch T. and Berg P., *Mol. Cell. Biol.*, 1986, 6, 2593–2601. The ISIS RG-1 vector contains the neomycin gene for G418 selection of stably transformed cells in culture and the ampicillin gene for bacterial amplification. Inserts can be directionally cloned by cutting at the Hind III and Xba I sites, releasing a stuffer fragment. The Hind III site is immediately 3' to the RSV promoter and the Xba I site is immediately 5' of the bovine growth hormone (BGH) poly (A) site. (see FIG. 1)

a. Random Sequences

A random population of oligonucleotides will be produced such that the 5' end of each oligomer consists of the Hind III site, d(CAAGCTTG). This is followed by approximately 25 nucleotide of random sequence, then the tail sequence d(TCTAGAGAAAAA) (SEQ ID NO: 7), creating an Xba I site and poly A tail. A primer complementary to the 3' end sequence, 5'd(TTTTTCTCTAGA)3' (SEQ ID NO: 8), will then be used as a primer for the synthesis of complementary strands to each of the random oligomers produced creating double strand molecules. The population of otigomers will then be subject digestion with Hind III and Xba I to give cohesive ends compatible with the ISIS RG-1 vector.

b. Random Genomic Fragments

Figure 2:
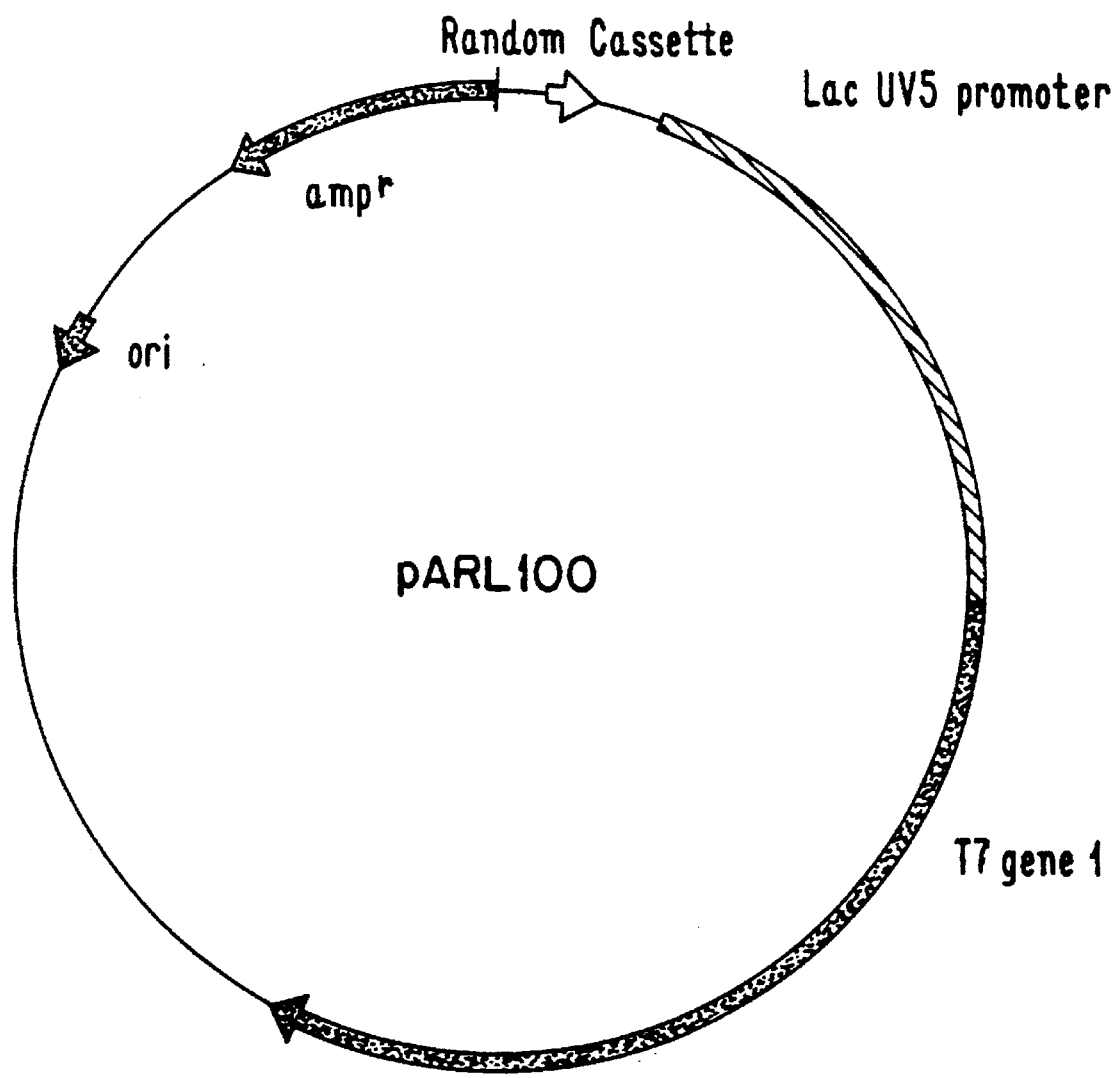
FIG. 2 is a schematic diagram of the vector pARL100.

The prepared vector with Hind III and XbaI ends will be filled with the Klenow fragment of DNA polymerase I, creating blunt ends. This will be followed by treatment with ligase to recircularize the molecule. This restores the Xba I site while eliminating the Hind III site. The vector is then cut with Xba I and the ends phosphatased to prevent recircularization. Insert will then be generated by cutting total genomic DNA with varying concentrations of DNAse I, and isolating the products of desired size on a preparative agarose gel. Ends of the sheared fragments will then be repaired with T7 DNA polymerase and Xba I linkers, d(GCTCTAGAGC) (SEQ ID NO: 9), blunt end ligated, followed by cutting the linked inserts with Xba I and cloning of the inserts directly into the vector.

c. cDNA Fragments mRNA will be isolated from cells infected with HSV. To directionally clone these sequences into the RG-1 vector, the poly A+ mRNA will be primed with a Hind III primer/adaptor d(CCAAGCTTGG(T)$_{15}$ (SEQ ID NO: 10). Following annealing of the primer, cDNA will be produced essentially as outlined by Gubler and Hoffmann, *Gene*, 1983, 25, 163 (FIG. 2). Once the efficiency of the constructions has been determined, the plasmids will be transfected as a population into CV-1 or HeLa cells using the method of Chen and Okayama, *Mol. Cell Biol.*, 1987, 7, 2745–2752. Stable transformants will be selected on the basis of resistance to G418. The population of stably transformed cells will then be infected with HSV. Surviving colonies express mRNA which is interacting to specifically block HSV infection. The plasmid DNA responsible for the effect can then be isolated from the transformed cells by PCR using Hind III and Xba I primers.

Example 2

Identification of random oligonucleotides which inhibit expression of the multidrug resistance-associated protein (MRP)

Acquired resistance to chemotherapy is a major problem in treatment of cancer by conventional cytotoxic drugs.

Tumors may initially respond well to chemotherapy but later become resistant to a variety of unrelated drugs, leading to relapse. One cause of multidrug resistance is believed to be overexpression of a member of the ATP-binding cassette transmembrane transporter superfamily known as multidrug resistance-associated protein (MRP). This protein is overexpressed in certain tumor cell lines, such as H69AR, which are multidrug resistant. Cole et al. (1992) Science 258:1650–1654; Slovak et al., (1993) Cancer Res. 53:3221–3225. MRP is expressed on the cell surface.

Synthesis of a random library.

The expression cassette, CCCAGGCCTTAATACGACT-CACTATAGGNNNNNNNNNNNNNNGCCCG-GACTCGGTTCGATTCCGAGTCCGGGCAC-CACATCGATGTC (SEQ ID NO: 1), was synthesized by standard phosphoramidite chemistry on an automated DNA synthesizer. The expression cassette encodes restriction sites at the 5' and 3' ends of the oligonucleotide, the T7 RNA polymerase promoter, an RNAse P1 recognition structure and a 14-base random sequence. The expression library contained a population of $2.7 \times 10^8$ sequences. A complementary strand to the expression cassette was synthesized using either Taq DNA polymerase or the Klenow fragment of DNA polymerase.

Selection, maintenance and transfection of multidrug resistant cell line H69AR cells.

H69AR, a doxorubicin-resistant human small cell lung carcinoma cell line, is selected and maintained as described in Mirski et al. (1987) Cancer Res. 47:2594–2598. Cells are transfected with the expression library using standard calcium phosphate methods. Positively transfected cells are selected by drug resistance.

Expression of oligoribonucleotides in vivo.

Oligonucleotides are expressed by inducing the RNA polymerase which directs the transcription of the random insert. Endogenous RNase P1 specifically terminates the transcript at the 3' end of the oligonucleotide.

Selection of cells containing active oligonucleotides which inhibit cell surface expression of MRP.

Selection of individual cells containing active oligonucleotide occurs when the cell population is treated with antibodies directed towards MRP and subsequently treated with complement. Hood, L. E., Weissman, I. L., and W. B. Wood. Immunology pp. 161–164; Benjamin/Cummings Publishing Co., Inc., 1978. The cell surface expression of MRP causes antibody-complement-mediated lysis of cells expressing MRP. Cells in which MRP expression has been inhibited by oligonucleotide are not affected. This allows the recovery of those cells in which expression of the MRP protein has been inhibited by oligonucleotide. These cells are then recovered and allowed to recover and expand in culture. The oligonucleotides contained within them are identified by plasmid isolation or PCR amplification and DNA sequencing of clonal populations of individual recovered cells using the Sanger dideoxy sequencing method.

Example 3

Identification of random oligonucleotides which inhibit the expression of a target gene in E. coli—the β-galactosidase gene Bacteria.

E. coli XL1-Blue MRF' (Δ(mcrA) 183, Δ(mcrCB-hsdSMR-mrr)173, endA1, supE44, thi-1, recA1, gyrA96, relA1, lac, [F proAB, lacqZΔM15, Tn10 (tet)']) was used as a host for transformations of the random library.

Synthesis of the random library.

The expression cassette, CCCAGGCCTTAATACGACT-CACTATAGGNNNNNNNNNNNNNNGCCCG-GACTCGGTTCGATTCCGAGTCCGGGCAC-CACATCGATGTC (SEQ ID NO: 1), was synthesized by standard phosphoramidite chemistry on an automated DNA synthesizer. The expression cassette encodes restriction sites at the 5' and 3' ends of the oligonucleotide, the T7 RNA polymerase promoter, an RNAse P1 recognition structure and a 14-base random sequence. The expression library contained a population of $2.7 \times 10^8$ sequences. A complementary strand to the expression cassette was synthesized using either Taq DNA polymerase or the Klenow fragment of DNA polymerase.

Cloning vector.

Figure 5:
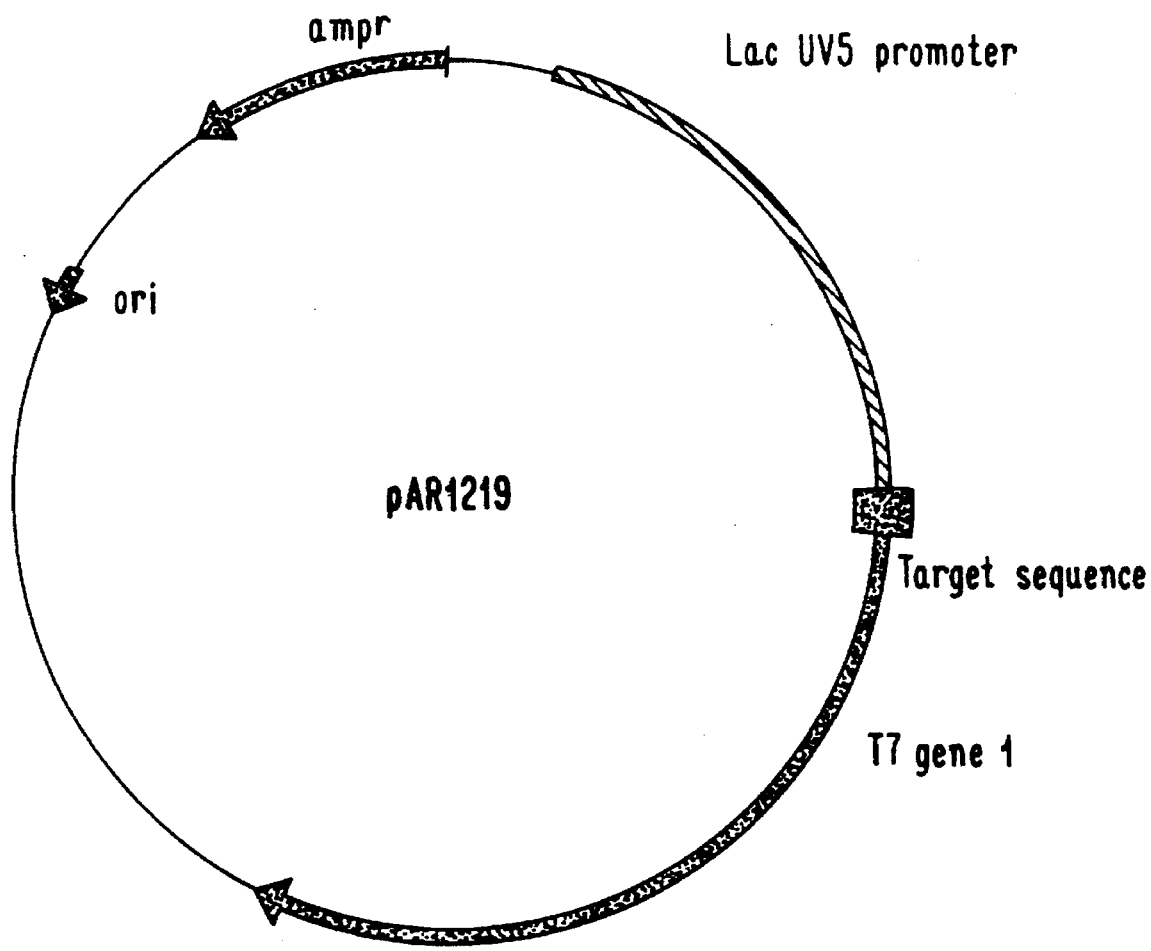
FIG. 5 is a schematic diagram of the vector pAR1219.

The prokaryotic expression vector pAR1219 was used. Davanloo, P., Rosenberg, A. H. Donn, J. J. and F. W. Studier. Proc. Natl. Acad. Sci. 81:2035–2039 (1984). This plasmid is shown in FIG. 5.

Ligation of the random library.

The double-stranded expression cassette was digested with restriction enzymes and cloned into the prokaryotic expression vector pAR1219 with T4 DNA ligase.

Transformation of E. coli.

The ligation reaction was transformed into the E. coli host, XL1-Blue MRF', using a modified calcium chloride shock protocol. Hanahan, D., J. Mol. Biol. 166:557–580 (1983). The transformed cell population was plated on LB agar plates supplemented with 50 μg/ml carbenicillin, IPTG and X-gal.

The expression of β-galactosidase is measured by measuring the ability of the host cell to process the exogenous substrate X-gal (5-bromo-4-chloro-3-indolyl-β-D-galactoside). A functional β-galactosidase enzyme confers a blue color to the host cell or colony in the presence of X-gal. Inhibition of the enzyme generates a white colony. After transformation and X-gal treatment, 102 colonies were obtained. Of these, 48 were blue, 45 were white and 9 were light blue. White colonies were picked and amplified. The expression vector was isolated from the white colonies by plasmid isolation and the random region of twelve of them was sequenced using the Sanger dideoxy sequencing method. Sanger, F., Nicklen, S. and A. R. Coulsen. Proc. Natl. Acad. Sci. 74:5463–5467 (1977). The sequences of the inserts are shown in Table 2:

TABLE 2

| | |
|---|---|
| SEQ ID NO: 11 | GGACTGCACGCGCGCG |
| SEQ ID NO: 12 | GGTGGTTATACGGCA- |
| SEQ ID NO: 13 | GGTGGTTATACGGCA- |
| SEQ ID NO: 14 | AGTCCCCCCATATTCA |
| SEQ ID NO: 15 | GGCTGGCGGGCCATAC |
| SEQ ID NO: 16 | GGTGTAAGAACGTCCA |
| SEQ ID NO: 17 | GGGAAACTATATCGTC |
| SEQ ID NO: 18 | GGTGCAGGTCAAGCCA |
| SEQ ID NO: 19 | GGTTGCCCTGATGAGG |
| SEQ ID NO: 20 | GGGCGTCGATGGCTAA |
| SEQ ID NO: 21 | GGCGCAACGAAGTTCC |
| SEQ ID NO: 22 | GGGTTTTAACAAGCAT |

The sequence of SEQ ID NO: 16 was compared to the predicted nucleic acid sequence of the β-galactosidase RNA target and 10 of the 14 bases were found to be complementary to the targeted RNA. These bases are underlined in Table 2.

What is claimed is:

1. A method for identifying an oligonucleotide which confers a desired phenotype comprising:

(a) inserting substantially random synthetic oligonucleotides into a plurality of expression vectors;

(b) transferring the vectors into cells;

(c) growing the cells under appropriate conditions for expression of the inserted oligonucleotides;

(d) assaying the cells for a desired phenotype conferred by an inserted oligonucleotide;

(e) identifying cells which have the desired phenotype; and (f) recovering a vector from a cell identified in step (e), thereby identifying an oligonucleotide which confers a desired phenotype.

2. The method of claim 1 further comprising determining the nucleic acid sequence of the oligonucleotide identified in step (f).

3. The method of claim 1 wherein the substantially random synthetic oligonucleotides are prepared through a solid phase synthetic technique.

4. The method of claim 3 wherein the substantially random synthetic oligonucleotides are about 6 to 100 nucleic acid subunits in length.

5. The method of claim 1 wherein the cells are mammalian cells.

6. The method of claim 5 wherein the desired phenotype is resistance to an infectious agent.

7. The method of claim 6 wherein the infectious agent is herpes simplex virus.

8. The method of claim 5 wherein the desired phenotype is decreased expression of a cell surface molecule.

9. The method of claim 8 a wherein the cell surface molecule is selected from the group consisting of intercellular adhesion molecules, oncogene products, multidrug resistance proteins and multidrug resistance-associated proteins.

10. The method of claim 9 wherein the oligonucleotide has activity against a target molecule selected from the group consisting of an activator protein, an activator nucleic acid, a responsive region and a promoter region.

11. The method of claim 1 wherein the cells are fungal cells.

12. The method of claim 11 wherein the desired phenotype is loss of adherence.

13. The method of claim 12 wherein the oligonucleotide reduces expression of an integrin.

14. The method of claim 1 wherein the cells are bacterial cells.

15. The method of claim 14 wherein the desired phenotype is loss of β-galactosidase activity.

16. The method of claim 15 wherein the oligonucleotide has a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12.

17. A method for identifying an oligonucleotide which hybridizes with nucleic acid of an infectious agent comprising:

(a) inserting substantially random synthetic oligonucleotides into a plurality of expression vectors;

(b) transferring the vectors into cells;

(c) infecting the cells with the infectious agent;

(d) growing the cells under appropriate conditions for expression of the inserted oligonucleotides and hybridization thereof to nucleic acid of the infectious agent;

(e) identifying cells which are resistant to the infection; and (f) recovering a vector from a cell identified in step (e), thereby identifying an oligonucleotide which hybridizes with nucleic acid of an infectious agent.

18. The method of claim 17 further comprising determining the nucleic acid sequence of the oligonucleotide identified in step (f).

19. The method of claim 17 wherein the substantially random synthetic oligonucleotides are prepared through a solid phase synthetic technique.

20. The method of claim 19 wherein the substantially random synthetic oligonucleotides are about 6 to 100 nucleic acid subunits in length.

21. The method of claim 17 wherein the cells are selected to be susceptible to infection by the infectious agent.

22. The method of claim 17 wherein the infectious agent is a herpesvirus and the cells are epithelial cells.

* * * * *

UNITED STATES PATENT AND TRADEMARK OFFICE
CERTIFICATE OF CORRECTION

PATENT NO. : 5,639,595
DATED : June 17, 1997
INVENTOR(S) : Mirabelli et al.

It is certified that error appears in the above-indentified patent and that said Letters Patent is hereby corrected as shown below:

Col. 1, line 49, please delete "tc" and insert therefor "to".
Col. 5, lines 13 and 14, please delete "otigonucleotides" and insert therefor "oligonucleotides".
Col. 7, line 41, please delete "aridine" and insert therefor "uridine".
Col. 11, line 29, please delete "vital" and insert therefor "viral".
Col. 14, line 25, please delete "otigomers" and insert therefor "oligomers".

Signed and Sealed this

Twenty-fourth Day of November, 1998

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 22

( 2 ) INFORMATION FOR SEQ ID NO: 1:

( i ) SEQUENCE CHARACTERISTICS:
( A ) LENGTH: 87
( B ) TYPE: nucleic acid
( C ) STRANDEDNESS: single
( D ) TOPOLOGY: linear ( x i ) SEQUENCE DESCRIPTION: SEQ ID NO: 1:

```
CCCAGGCCTT AATACGACTC ACTATAGGNN NNNNNNNNN NNGCCCGGAC          50
TCGGTTCGAT TCCGAGTCCG GGCACCACAT CGATGTC                       87
```

( 2 ) INFORMATION FOR SEQ ID NO: 2:

( i ) SEQUENCE CHARACTERISTICS:
( A ) LENGTH: 102
( B ) TYPE: nucleic acid
( C ) STRANDEDNESS: single
( D ) TOPOLOGY: linear ( x i ) SEQUENCE DESCRIPTION: SEQ ID NO: 2:

```
CCCAGGCCTT AATACGACTC ACTATAGGNN NNNNNNNNN NNCGGTCTCA          50
CGAGCAAAAG CTCGTCTGAT GAGTCCGTGA GGACGAAAGA CCGATCGATG TC     102
```

( 2 ) INFORMATION FOR SEQ ID NO: 3:

( i ) SEQUENCE CHARACTERISTICS:
( A ) LENGTH: 93
( B ) TYPE: nucleic acid
( C ) STRANDEDNESS: single
( D ) TOPOLOGY: linear ( x i ) SEQUENCE DESCRIPTION: SEQ ID NO: 3:

```
CCCAGGCCTT AATACGACTC ACTATAGGNN NNNNNNNNN NNAATAAAGC          50
CCGGACTCGG TTCGATTCCG AGTCCGGGCA CCACATCGAT GTC                93
```

( 2 ) INFORMATION FOR SEQ ID NO: 4:

( i ) SEQUENCE CHARACTERISTICS:
( A ) LENGTH: 28
( B ) TYPE: nucleic acid
( C ) STRANDEDNESS: single
( D ) TOPOLOGY: linear ( x i ) SEQUENCE DESCRIPTION: SEQ ID NO: 4:

```
CCCAGGCCTT AATACGACTC ACTATAGG                                 28
```

( 2 ) INFORMATION FOR SEQ ID NO: 5:

( i ) SEQUENCE CHARACTERISTICS:
( A ) LENGTH: 45
( B ) TYPE: nucleic acid
( C ) STRANDEDNESS: single
( D ) TOPOLOGY: linear ( x i ) SEQUENCE DESCRIPTION: SEQ ID NO: 5:

```
GCCCGGACTC GGTTCGATTC CGAGTCCGGG CACCACATCG ATGTC              45
```

( 2 ) INFORMATION FOR SEQ ID NO: 6:

(i) SEQUENCE CHARACTERISTICS:
    (A) LENGTH: 51
    (B) TYPE: nucleic acid
    (C) STRANDEDNESS: single
    (D) TOPOLOGY: linear (xi) SEQUENCE DESCRIPTION: SEQ ID NO: 6:

AATAAAGCCC GGACTCGGTT CGATTCCGAG TCCGGGCACC ACATCGATGT         50

C                                                              51

(2) INFORMATION FOR SEQ ID NO: 7:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 7:

TCTAGAGAAA AA                                                  12

(2) INFORMATION FOR SEQ ID NO: 8:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 8:

TTTTTCTCTA GA                                                  12

(2) INFORMATION FOR SEQ ID NO: 9:

(i) SEQUENCE CHARACTERISTICS:
        (A) LENGTH: 10
        (B) TYPE: nucleic acid
        (C) STRANDEDNESS: single
        (D) TOPOLOGY: linear (xi) SEQUENCE DESCRIPTION: SEQ ID NO: 9:

GCTCTAGAGC                                                     10

(2) INFORMATION FOR SEQ ID NO: 10:

(i) SEQUENCE CHARACTERISTICS:
        (A) LENGTH: 25
        (B) TYPE: nucleic acid
        (C) STRANDEDNESS: single
        (D) TOPOLOGY: linear (xi) SEQUENCE DESCRIPTION: SEQ ID NO: 10:

CCAAGCTTGG TTTTTTTTTT TTTTT                                    25

(2) INFORMATION FOR SEQ ID NO: 11:

(i) SEQUENCE CHARACTERISTICS:
        (A) LENGTH: 16
        (B) TYPE: nucleic acid
        (C) STRANDEDNESS: single
        (D) TOPOLOGY: linear (xi) SEQUENCE DESCRIPTION: SEQ ID NO: 11:

GGACTGCACG CGCGCG         16

(2) INFORMATION FOR SEQ ID NO: 12:

( i ) SEQUENCE CHARACTERISTICS:
    ( A ) LENGTH: 15
    ( B ) TYPE: nucleic acid
    ( C ) STRANDEDNESS: single
    ( D ) TOPOLOGY: linear ( x i ) SEQUENCE DESCRIPTION: SEQ ID NO: 12:

GGTGGTTATA CGGCA        15

( 2 ) INFORMATION FOR SEQ ID NO: 13:

( i ) SEQUENCE CHARACTERISTICS:
    ( A ) LENGTH: 15
    ( B ) TYPE: nucleic acid
    ( C ) STRANDEDNESS: single
    ( D ) TOPOLOGY: linear ( x i ) SEQUENCE DESCRIPTION: SEQ ID NO: 13:

GGTGGTTATA CGGCA        15

( 2 ) INFORMATION FOR SEQ ID NO: 14:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: linear ( x i ) SEQUENCE DESCRIPTION: SEQ ID NO: 14:

AGTCCCCCCA TATTCA       16

( 2 ) INFORMATION FOR SEQ ID NO: 15:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: linear ( x i ) SEQUENCE DESCRIPTION: SEQ ID NO: 15:

GGCTGGCGGG CCATAC       16

( 2 ) INFORMATION FOR SEQ ID NO: 16:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: linear ( x i ) SEQUENCE DESCRIPTION: SEQ ID NO: 16:

GGTGTAAGAA CGTCCA       16

( 2 ) INFORMATION FOR SEQ ID NO: 17:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: linear ( x i ) SEQUENCE DESCRIPTION: SEQ ID NO: 17:

GGGAAACTAT ATCGTC       16

( 2 ) INFORMATION FOR SEQ ID NO: 18:

( i ) SEQUENCE CHARACTERISTICS:
    ( A ) LENGTH: 16

( B ) TYPE: nucleic acid
( C ) STRANDEDNESS: single
( D ) TOPOLOGY: linear ( x i ) SEQUENCE DESCRIPTION: SEQ ID NO: 18:

GGTGCAGGTC AAGCCA    16

( 2 ) INFORMATION FOR SEQ ID NO: 19:

( i ) SEQUENCE CHARACTERISTICS:
( A ) LENGTH: 16
( B ) TYPE: nucleic acid
( C ) STRANDEDNESS: single
( D ) TOPOLOGY: linear ( x i ) SEQUENCE DESCRIPTION: SEQ ID NO: 19:

GGTTGCCCTG ATGAGG    16

( 2 ) INFORMATION FOR SEQ ID NO: 20:

( i ) SEQUENCE CHARACTERISTICS:
( A ) LENGTH: 16
( B ) TYPE: nucleic acid
( C ) STRANDEDNESS: single
( D ) TOPOLOGY: linear ( x i ) SEQUENCE DESCRIPTION: SEQ ID NO: 20:

GGGCGTCGAT GGCTAA    16

( 2 ) INFORMATION FOR SEQ ID NO: 21:

( i ) SEQUENCE CHARACTERISTICS:
( A ) LENGTH: 16
( B ) TYPE: nucleic acid
( C ) STRANDEDNESS: single
( D ) TOPOLOGY: linear ( x i ) SEQUENCE DESCRIPTION: SEQ ID NO: 21:

GGCGCAACGA AGTTCC    16

( 2 ) INFORMATION FOR SEQ ID NO: 22:

( i ) SEQUENCE CHARACTERISTICS:
( A ) LENGTH: 16
( B ) TYPE: nucleic acid
( C ) STRANDEDNESS: single
( D ) TOPOLOGY: linear ( x i ) SEQUENCE DESCRIPTION: SEQ ID NO: 22:

GGGTTTTAAC AAGCAT    16